United States Patent
Ravichandran et al.

(10) Patent No.: US 9,486,605 B2
(45) Date of Patent: Nov. 8, 2016

(54) INTRODUCER SHEATH WITH BRAIDED FILAMENT SECUREMENT MECHANISM

(75) Inventors: Mahendran Ravichandran, Mundelein, IL (US); Kurt J. Tekulve, Ellettsville, IN (US); Michael D. Deckard, Solsberry, IN (US); Michelle Reynolds, Bloomington, IN (US)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 1170 days.

(21) Appl. No.: 13/534,240

(22) Filed: Jun. 27, 2012

(65) Prior Publication Data

US 2013/0018318 A1 Jan. 17, 2013

Related U.S. Application Data

(60) Provisional application No. 61/508,350, filed on Jul. 15, 2011.

(51) Int. Cl.
*A61M 25/00* (2006.01)
*A61M 25/01* (2006.01)

(52) U.S. Cl.
CPC ....... *A61M 25/005* (2013.01); *A61M 25/0012* (2013.01); *A61M 25/0053* (2013.01); *A61M 25/0108* (2013.01); *A61M 2025/0059* (2013.01)

(58) Field of Classification Search
CPC ......... A61M 25/005; A61M 25/0012; A61M 25/0053; A61M 25/0108; A61M 2025/0059
See application file for complete search history.

(56) References Cited

U.S. PATENT DOCUMENTS

| | | | |
|---|---|---|---|
| 4,817,613 A * | 4/1989 | Jaraczewski | A61M 25/0012 138/125 |
| 5,005,755 A | 4/1991 | Takahashi et al. | |
| 5,283,082 A | 2/1994 | Hussmann et al. | |
| 5,380,304 A | 1/1995 | Parker | |
| 5,603,705 A | 2/1997 | Berg | |
| 5,951,495 A | 9/1999 | Berg et al. | |
| 6,505,066 B2 | 1/2003 | Berg et al. | |
| 6,562,022 B2 | 5/2003 | Hoste et al. | |
| 7,597,830 B2 | 10/2009 | Zhou | |
| 2001/0034514 A1 | 10/2001 | Parker | |
| 2002/0032408 A1 | 3/2002 | Parker et al. | |
| 2010/0004631 A1 * | 1/2010 | Zhou | A61L 29/085 604/527 |
| 2010/0016837 A1 * | 1/2010 | Howat | A61M 25/0012 604/527 |

* cited by examiner

*Primary Examiner* — Emily Schmidt
*Assistant Examiner* — Lauren M Peng
(74) *Attorney, Agent, or Firm* — Brinks Gilson & Lione

(57) ABSTRACT

A tubular body for a medical device for insertion within a body passageway of a patient. The tubular body includes a tubular inner liner. A braided member is disposed along an outer surface of the liner. The braided member includes intersecting filaments and cells defined by the filaments. A securement mechanism, such as radiopaque solder, is disposed along a circumferential region of the braided member. The securement mechanism is attached to portions of the filaments and spans the cells that correspond to the circumferential region to inhibit relative movement of filament ends. An outer surface of the securement mechanism is sized to extend radially outward to a position up to an outer surface of the braided member to not add to the overall wall thickness of the tubular body. An outer jacket is positioned longitudinally around the braided member and connected to the inner liner.

14 Claims, 6 Drawing Sheets

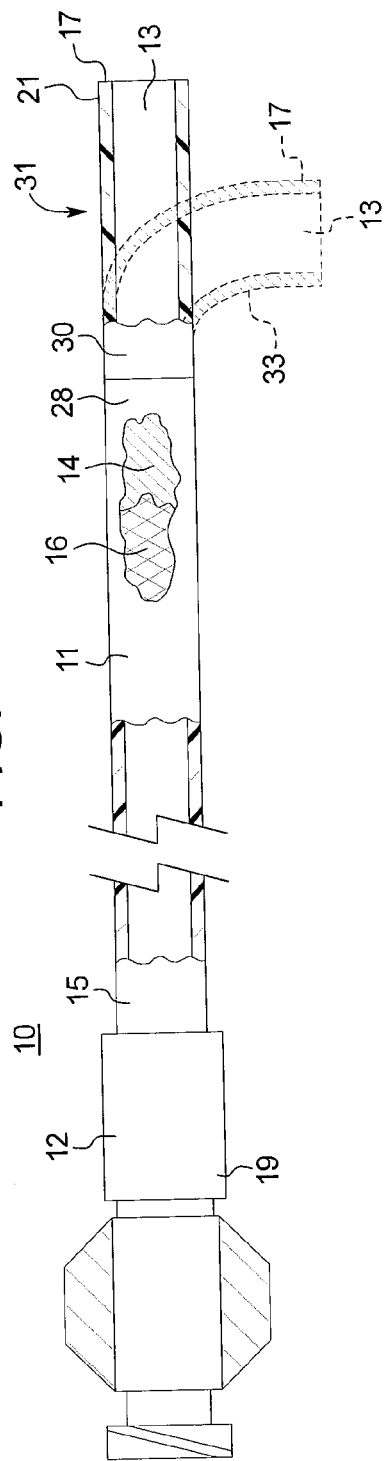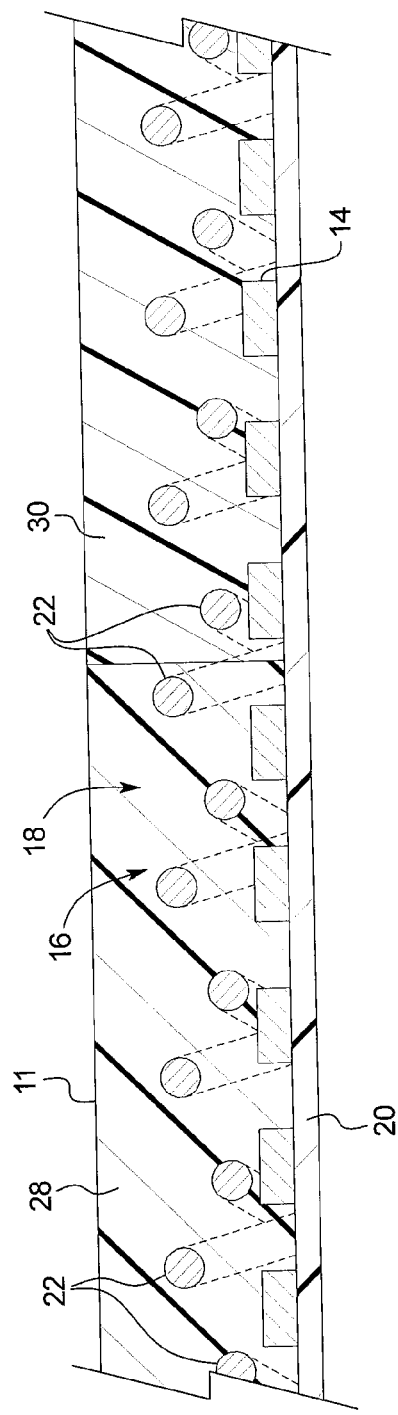

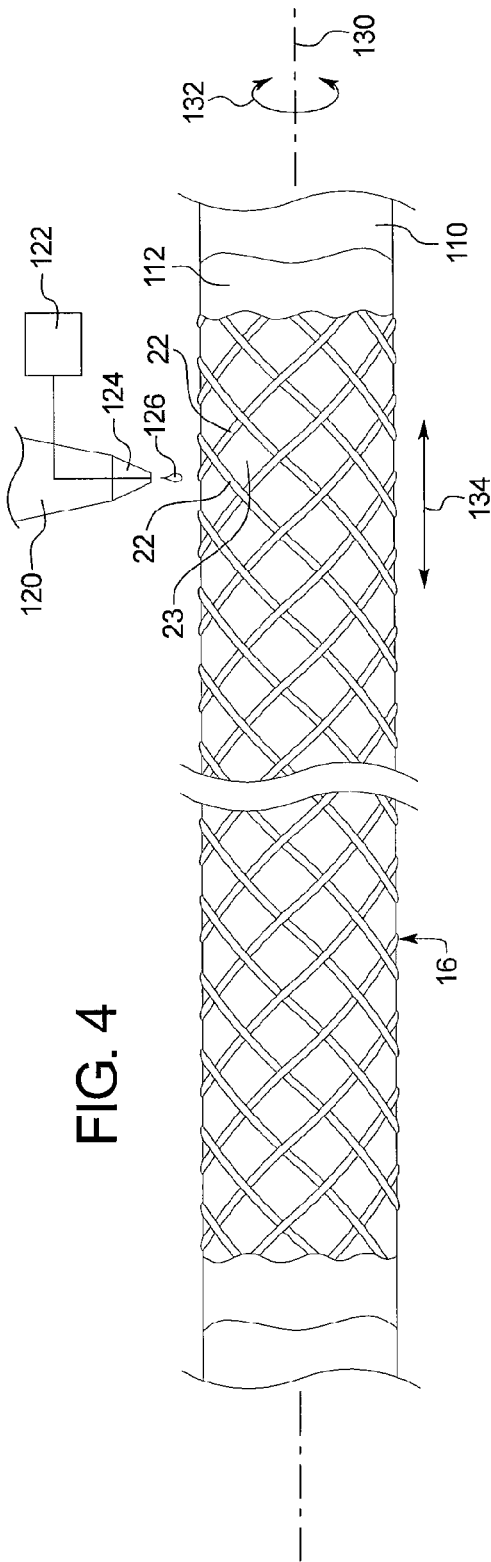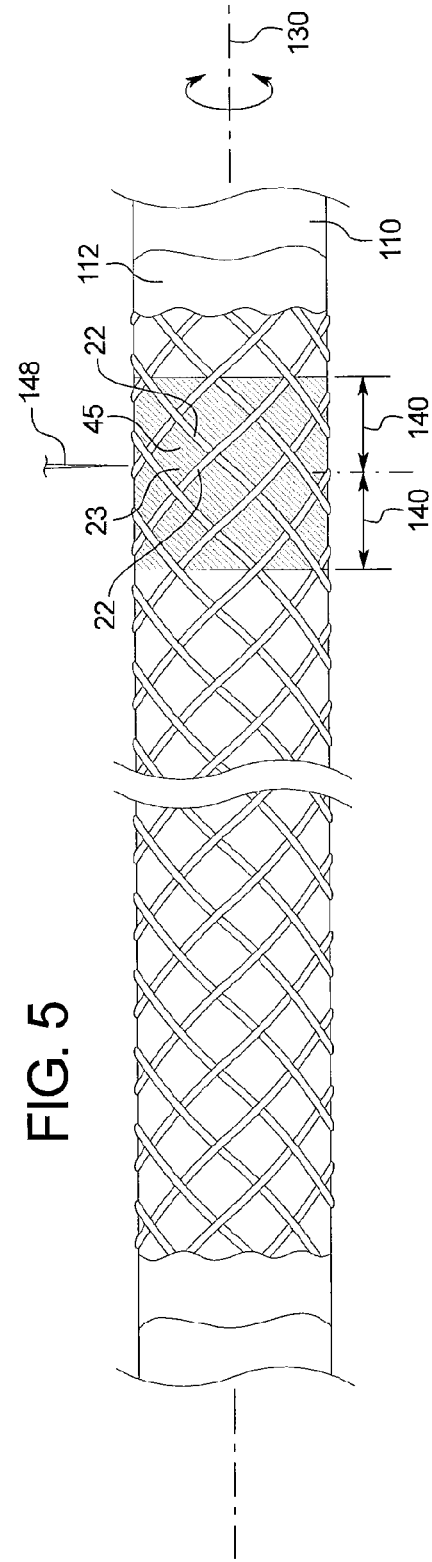

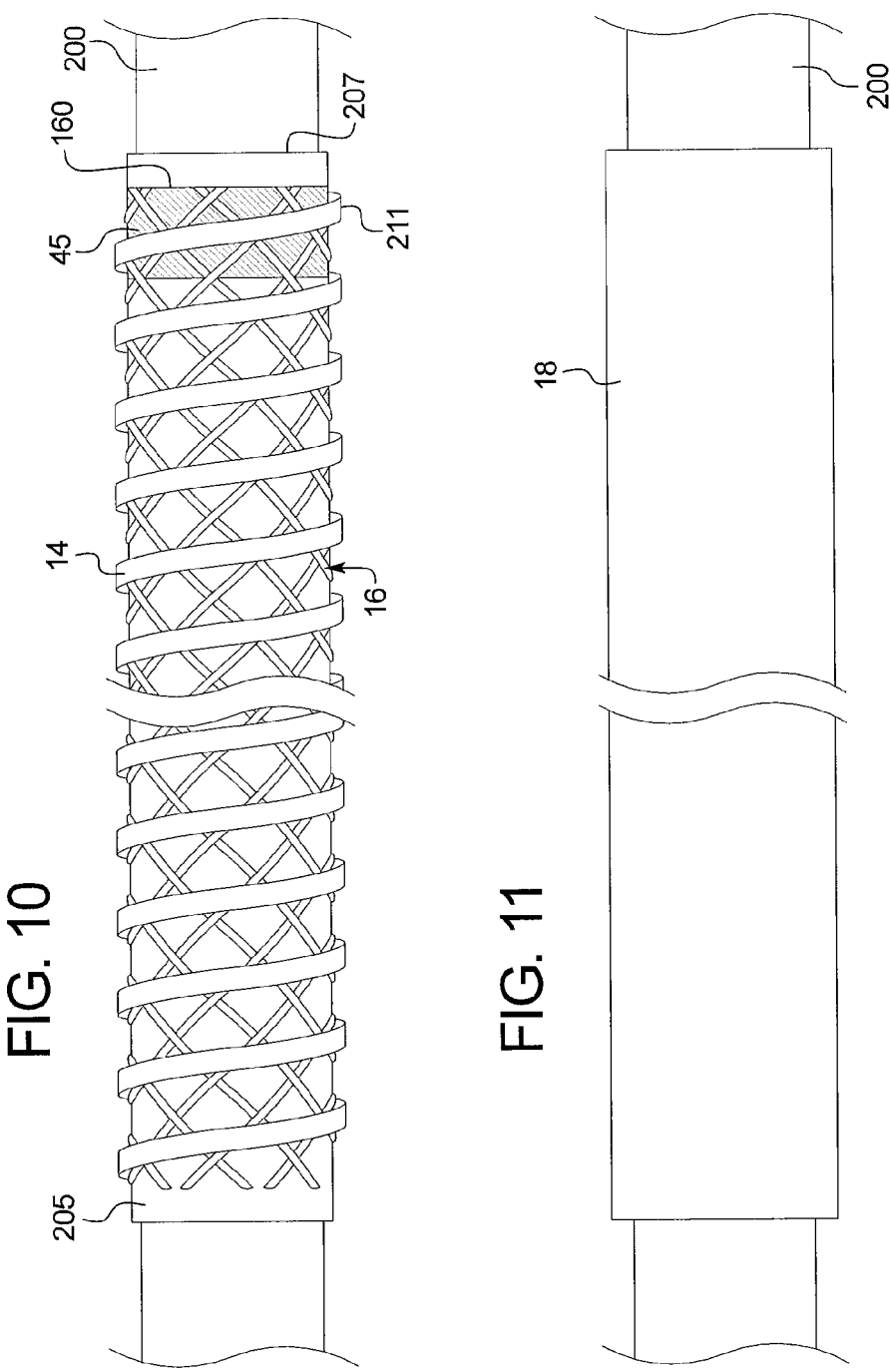

INTRODUCER SHEATH WITH BRAIDED FILAMENT SECUREMENT MECHANISM

This application claims priority to U.S. Provisional Application No. 61/508,350, filed Jul. 15, 2011, which is hereby incorporated by reference herein.

BACKGROUND

This present disclosure relates to the field of medical devices, and more particularly, to devices such as sheaths, catheters, or tubes with a mechanism to secure a braided filament.

Numerous advances of considerable note have occurred in medical surgical techniques over the last few decades. Among the most significant advances has been the adoption, and now-routine performance, of a wide variety of minimally invasive procedures. Non-limiting examples of such procedures include angioplasty, endoscopy, laparoscopy, and arthroscopy. These minimally invasive procedures can be distinguished from conventional open surgical procedures in that access to a site of concern within a patient is achieved through a relatively small incision, into which a tubular device (or tubular portion of a device) is inserted or introduced. The tubular device, or device portion, keeps the incision open while permitting access to the target site via the interior (i.e., lumen) of the tubular device. Body passageways in which medical interventional devices are now commonly introduced include the esophagus, trachea, colon, biliary tract, urinary tract, and vascular system, among other locations within the body. One particularly significant example of a minimally invasive technique involves the temporary or permanent implantation of a medical interventional device, such as a stent, into a passageway in the body of a patient.

When placing the medical interventional device, communication with the passageway is typically attained by inserting an access device, such as an introducer sheath, into the body passageway. One typical procedure for inserting the introducer sheath is the well-known Seldinger percutaneous entry technique. In the Seldinger technique, a needle is initially inserted into the passageway, such as a vessel, and a wire guide is inserted into the vessel through a bore of the needle. The needle is withdrawn, and an introducer assembly is inserted over the wire guide into the opening in the vessel.

Typically, the introducer assembly includes an outer introducer sheath, and an inner dilator having a tapered distal end. The tapered end of the dilator stretches the opening in the vessel in controlled fashion, so that introduction of the larger diameter introducer sheath may then be carried out with a minimum of trauma to the patient. Following satisfactory placement of the introducer sheath, the dilator is removed, leaving at least the distal portion of the larger diameter introducer sheath in place in the vessel. The interventional device, such as an expandable stent, etc., may then be inserted through the introducer sheath for placement at a target site within the vasculature. Alternatively, the stent may be placed at the target site by withdrawing the introducer sheath from around the constricted stent. In either technique, upon placement at the target site, the stent expands to the diameter of the vessel.

Historically, percutaneous insertion techniques were problematic, due at least in large part to the lack of flexibility and/or kink resistance of the sheath. Early sheaths were typically formed of a relatively stiff fluorocarbon, such as polytetrafluoroethylene (PTFE) or fluorinated ethylene propylene (FEP). The sheaths were typically of thin-walled construction, and were prone to kinking, particularly when threaded through tortuous pathways within the body. Increasing the thickness of the sheath only minimally improved the kink resistance of the sheath. At the same time, the added thickness occupied valuable space in the vessel, thereby minimizing the diameter of the interventional device that could be passed therethrough. In addition, increasing the thickness of the sheath necessitated the use of a larger entry opening than would otherwise be required.

A kinked sheath is essentially unusable, and generally cannot be straightened while positioned in the body of the patient. Consequently, once a sheath kinks, the sheath must be removed from the vessel, leaving an enlarged, bleeding opening which cannot generally be reused. Access to the vessel must then be re-initiated at an alternative site, and the process repeated with a new sheath. In some cases, a suitable alternative site is not available, and the percutaneous procedure must be abandoned altogether in favor of a different, and often more intrusive, technique.

In recent years, introducer sheaths have been improved in order to enhance their flexibility and kink resistance. Such sheaths are now routinely used to percutaneously access sites in the patient's anatomy that previously could not be accessed with existing sheaths, or that could be accessed only upon the exercise of an undesirable amount of trial and error, with the concomitant discard of sheaths whose placement had been unsuccessful.

Many newer sheaths exhibit a much higher degree of kink resistance than was achievable with prior art sheaths. One example of a flexible, kink resistant introducer sheath is described in U.S. Pat. No. 5,380,304 ("the '304 patent"), which is incorporated herein by reference in its entirety. Here, the sheath described therein includes a lubricious inner liner having a helical coil fitted over the liner. An outer tube is connected to the outer surface of the liner through the coil turns. The coil reinforcement imparts kink resistant to this thin-walled sheath through a wide range of bending.

Another example introducer sheath is described in U.S. Patent Publication No. 2001/0034514 ("the '514 Publication"), which is incorporated herein by reference in its entirety. The sheath described therein is similar in many respects to the sheath of the '304 patent, and is formed such that the proximal end of the sheath has a higher stiffness, while the distal end has a lower stiffness. Since the distal end of the sheath has a lower stiffness (and therefore is more flexible) than the proximal end, the sheath is able to traverse portions of the anatomy that would have been difficult, if not impossible, to traverse with stiffer sheaths. Since the proximal end has a higher stiffness (and is therefore less flexible) than the distal end, the sheath maintains the trackability to traverse tortuous areas of the anatomy. This presence of the coil reinforcement also enables this sheath to be kink resistant through a wide range of bending angles.

Unfortunately, sheaths having a coil can exhibit poor pushability due to axial stretching or compression and exhibit poor torqueability during use. To enhance torqueability and pushability, some introducer sheaths have included a braid, as well as a braid and a coil in the wall of its shaft. Such construction of the sheath is described in U.S. Patent Publication No. 2002/0032408 ("the '408 Publication"), which is incorporated herein by reference in its entirety.

Notwithstanding the benefits that have been achieved by the use of such introducer sheaths, new challenges continue to be faced. For example, during manufacturing of the introducer sheath with a braid, the ends of filaments that define the braid can fray open and poke through the outer layers of the introducer sheath. The ends may also extend inward and poke through the inner liner into the passageway of the sheath. In some instances, the braid filaments will tend to unravel during manufacturing. Consequently, the current processes for controlling the fraying of the braid, such as annealing, still results in many manufacturing rejects.

It is desired to provide an improved introducer apparatus suitable for traversing tortuous passageways in the patient's anatomy, and that is capable of minimizing the problems of the prior art. More particularly, it is desired to provide a braided member configuration within an introducer sheath that is capable of minimizing fraying of the braid end, thereby reducing manufacturing rejects. It would be desirable to reduce the fraying of the braid end without contributing additional thickness to the sheath wall to ensure the sheath wall is as thin as possible.

BRIEF SUMMARY

The problems of the prior art are addressed by the features of the following examples. In one form thereof, a tubular body for a medical device can include a tubular inner liner and a braided member. The braided member can be disposed along the outer surface of the inner liner. The braided member can have a proximal end and a distal end, and can include a plurality of intersecting filaments and a plurality of cells defined by the intersecting filaments. The braided member can have a braided filament securement mechanism disposed along a circumferential region located at the distal end of the braided member. The securement mechanism can be configured to inhibit relative movement of filament ends. The securement mechanism can be attached to portions of the filaments to span the cells that correspond to the circumferential region. The outer surface of the braided member is positioned at or beyond the outer surface of the securement mechanism. An outer jacket can be positioned longitudinally around the braided member to connect to the inner liner. In one aspect, the securement mechanism includes a radiopaque solder material. In another aspect, multiple circumferential regions can include the radiopaque solder material, where the circumferential regions are axially spaced from one another at regular intervals.

In another form thereof, an introducer sheath includes an inner liner, a braided member, and a coiled member. The braided member can be disposed along the outer surface of the inner liner. The braided member can include a plurality of intersecting filaments and a plurality of cells defined by the intersecting filaments. A braided filament securement mechanism can be disposed along a circumferential region of the braided member and configured to inhibit relative movement of the ends of the filaments. The thickness of the securement mechanism is sized to fit between the outer and inner surfaces of the braided member. The securement mechanism can include a radiopaque solder that is rigidly fused to portions of the filaments and spans the cells that correspond to the circumferential region. The coiled member can be disposed along the outer surface of the inner liner. An outer jacket can be positioned longitudinally around the braided member, and connected to the inner liner. In one aspect, the securement mechanism can be disposed along a distal region of the sheath, which is movable between an arcuate configuration and a linear configuration.

In yet another form thereof, a method for manufacturing a tubular body for a medical device is provided. The method can include one or more of the following steps. A solder can be applied to a circumferential region of a braided member for an axial length. The braided member can include a plurality of intersecting filaments and a plurality of cells defined by the intersecting filaments. The solder can rigidly fuse portions of the intersecting filaments and can span the cells. The outer surface of the solder is sized to extend radially outward to a position up to an outer surface of the braided member. The braided member can be positioned over at least a portion of an inner liner tube. An outer layer jacket can be secured over the inner liner tube and the braided member. Portions of the solder can be removed so that the outer surface of the braided member extends at least beyond the outer surface of the solder.

BRIEF DESCRIPTION OF THE DRAWINGS

FIG. 1 is a side view, partially in section, of an example medical device;

FIG. 2 is a partial longitudinal cross-sectional view of a partial portion of the wall of the medical device of FIG. 1;

FIG. 4 is a side view of a braided member disposed over a mandrel, depicting an example application of a braided filament securement mechanism;

FIG. 5 is a side view of the braided member disposed over the mandrel of FIG. 4, depicting an example cutting operation of a braided filament securement mechanism;

FIGS. 8-11 are side views of exemplary method steps used to manufacture the medical device of FIG. 1.

DETAILED DESCRIPTION OF THE DRAWINGS AND THE PRESENTLY PREFERRED EMBODIMENTS

Figure 3A:
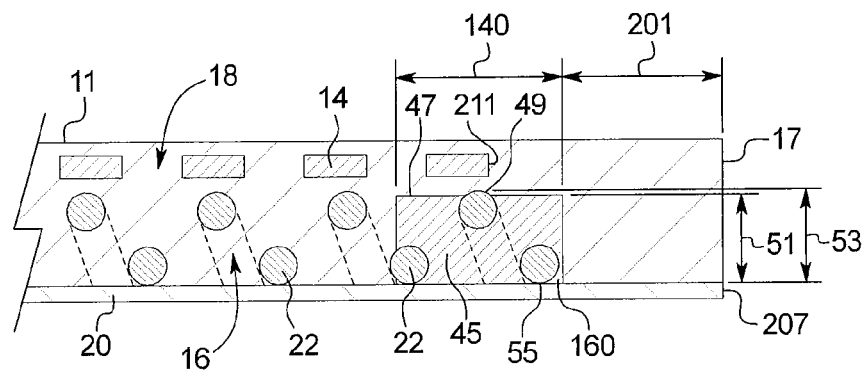
FIG. 3A is a partial longitudinal cross-sectional view of a partial portion of the wall of another example medical device with a braided filament securement mechanism.

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. It is understood that like-referenced numerals are used throughout the Figures to designate similar components.

In the following discussion, the terms "proximal" and "distal" will be used to describe the opposing axial ends of the inventive apparatus, as well as the axial ends of various component features. The term "proximal" is used in its conventional sense to refer to the end of the apparatus (or component thereof) that is closest to the operator during use of the apparatus. The term "distal" is used in its conventional sense to refer to the end of the apparatus (or component thereof) that is initially inserted into the patient, or that is closest to the patient during use.

In FIG. 1, an example medical device 10 useful for performing any of a variety of minimally invasive medical procedures, including angioplasty, diagnosis, chemotherapy, drainage, endoscopy, laparoscopy, arthroscopy, and the guiding or introduction of other devices into a patient is illustrated. In its simplest form, the medical device 10 is a simple guide, diagnostic, infusion or drainage catheter or introducer sheath, which will be referred to throughout the specification as an introducer sheath 12.

The introducer sheath 12 includes a tubular sheath body 11 having a passageway 13 that extends longitudinally therethrough. The tubular body 11 includes a proximal portion 15, and a distal portion 17 for initial insertion into the body passageway. In the non-limiting embodiment shown, the end of the proximal portion 15 of the tubular body 11 is receivable in a base structure 19. Those skilled in the art will appreciate that the base structure 19 can include various conventional proximal attachments, such as a hub assembly or a multi-chamber manifold.

FIGS. 2-3A are longitudinal cross-sectional views of a partial portion of differently constructed tubular sheath walls. These figures best illustrate the layered structure of the sheath wall, and the relative positions of one or more reinforcing members. Two reinforcing members, namely a coiled member 14 and a braided member 16, are disposed along at least partially the length of the body 11 in a manner to be described. If desired, a conventional radiopaque marker band 21 may be incorporated into the distal end 17 of the sheath in well-known fashion.

The coiled member 14 may comprise a medical grade metal or metal alloy, such as stainless steel, or a shape memory composition such as nitinol. Alternatively, the coiled member 14 may be formed from other medical grade materials known in the art to be suitable for such use, such as polymers and composite materials. In one example, the coiled member 14 is formed from flat wire as shown in FIG. 2, although a coiled member formed from other compositions and having other cross-sections such as circular or elliptical may be substituted in an appropriate case. As described herein, the coiled member 14 may be wrapped, wound, compression fitted, or otherwise applied around an inner liner, if employed, in conventional fashion. In one example, the coiled member can be in a stressed, radially expanded condition, such as described in the previously incorporated '408 Publication. Coils are well-known reinforcements for medical devices, and those skilled in the art are well aware of other suitable techniques for applying a coiled member to a tubular member for medical applications.

The braided member 16 may extend over (FIG. 2) or under (FIG. 3A) at least part of the coiled member 14. The braided member 16 comprises a plurality of intersecting filaments 22 of circular, flat, elliptical, or other conventional wire cross-section (circular being illustrated in FIG. 2). The braided member 16 can be formed of medical grade metal or metal alloy. Non-limiting examples of such materials include stainless steel, shape memory alloys such as nitinol, a nickel-titanium alloy, or precious metals such as gold and silver. Those skilled in the art will appreciate that the braided member 16 may alternatively be formed of other medical grade materials known in the art to be suitable for such use, such as polymers and composite materials. The braided member 16 may be formed with varied numbers and pitches of intersected filaments, which the number of filaments and pitch may be varied within segments of a particular sheath, all in accordance with known techniques. As with coiled members, the braided members are also well-known reinforcements for medical devices, and those skilled in the art are well aware of suitable techniques for applying a braided member to a tubular member for medical applications.

Although braided and coiled members are now routinely used as reinforcements in tubular medical devices, those skilled in the art recognize that these reinforcements are not generally considered interchangeable. Rather, each is generally preferred in order to address a particular condition likely to be encountered by the sheath during introduction into a body opening. For example, a coiled member is typically utilized in a sheath to minimize the possibility of the sheath kinking and/or to minimize ovalization of the sheath lumen during bending of the sheath. The braided member, on the other hand, is typically utilized when it is desired to impart stiffness, pushability, and/or torqueability to the sheath. Such properties are advantageous when maneuvering a lengthy sheath into remote anatomy. A braided member, however, is not generally capable of providing the type of kink resistance available with a coiled member. Similarly, a coiled member is not generally capable of providing the type of pushability or torqueability available with a braided member. Although each of these types of reinforcements has its advantages as described, the ability to resist kinking and ovalization throughout a large bending radius is often considered a paramount property of a sheath. This is particularly true in the vicinity of the distal end of the sheath. For this reason, it is believed that most presently-available commercial introducer sheaths include a coil reinforcement. Examples of such sheaths having coil reinforcements are described in the incorporated-by-reference patent documents recited hereinabove. Since the proximal portion can have a higher stiffness (and therefore less flexible) than the distal portion, the sheath maintains the trackability to traverse tortuous areas of the anatomy.

According to FIGS. 2-3A, the body 11 can include a polymeric outer layer jacket 18 positioned over and contacting the coiled member 14, the braided member 16, or both. The outer layer 18 can maintain the coiled member 14 in its position, such as, e.g., in a stressed, radially expanded condition, by adhesion to the coiled member 14, for example, by thermally bonding to the coiled member 14. In one example, the outer layer 18 may be formed of any well-known polymer commonly used for such purpose. In one example, the outer layer 18 comprises a heat formable polyamide material, such as nylon, a polyether block amide (PEBA), or polyurethane. This heat formable material melts upon heating, such that portions flow between the respective cells of the braided member or the turns of the coiled member, and bond to the outer surface, which is preferably roughened, of an inner liner, if employed.

Any particular portion of the tubular body 11 can be given a flexibility or springiness which is different from the flexibility or springiness of the remainder of the body 11. There are several ways in which this difference can be achieved. In one example, the thickness of the outer layer 18 can be varied along the length of the body 11. In another example, the outer layer 18 can be formed from at least two discrete longitudinal segments (such as the proximal segment 28 and the distal segment 30) of differing durometer. Making the distal segment 30 of the outer layer 18 from a softer material than that from which the proximal segment 28 is made yields a tubular body 11 that has a more flexible or springier tip than the balance of the body 11. In another example, the coiled member may extend distally beyond the distal end of the braided member or vice versa. This leaves a distal portion of the coiled member or braided member, which is not covered by the other of the braided member or coiled member, and similarly yields a tubular body having a more flexible or springier tip than the balance of the sheath body.

In FIGS. 2-3A, the tubular body 11 may include an inner liner 20. Without regard to whether the tubular body 11 comprises the inner liner 20, the body 11 has the passageway 13 extending longitudinally therethrough. The passageway 13 can receive a conventional guide wire (not shown) therein, or the passageway 13 can be intended for the delivery of a diagnostic or therapeutic fluid, or the removal of a fluid from the patient.

The inner liner 20 may be beneath and in contact with at least part of the coiled member (FIG. 2) and/or the braided member (FIG. 3A). The inner liner 20 can include a lubricious material to allow for easy insertion and withdrawal of the medical interventional device, and more preferably, a fluoropolymer of the type commonly used to impart strength and lubricity to a medical device. Most preferably, the fluoropolymer comprises polytetrafluoroethylene (PTFE). Lubricious inner liners for sheaths are well known in the medical arts, and those skilled in the art can readily select an appropriate liner for a particular use. The inner surface of the inner liner 20 can also be smooth and nonporous for minimizing the formation of blood clots and other thrombi thereon. The wall of the inner liner 20 may have sufficient radial rigidity to prevent the filaments of the braided member 16 and/or the turns of the coiled member 14 from protruding into the passageway 13.

It is envisioned that the inner liner can have a uniform inside diameter ranging up to about 30 French (10 mm), or even higher in some instances, thereby allowing passage of the largest possible diameter medical interventional device therethrough. The wall thickness of the inner liner will typically range between about 0.001 and 0.003 inch (0.0254 and 0.076 mm), and is preferably about 0.0015 inch (0.038 mm). Even larger, or smaller, wall thicknesses may be appropriate in a particular case. Those skilled in the art will appreciate that all dimensions recited herein are exemplary only, and that the apparatus described herein may be constructed to be of any size necessary and appropriate to accomplish the purposes for which the sheath is to be employed.

As shown in FIG. 1, in one example the sheath can have a distal tip region 31 that is linear in form and that is elongate such as, e.g., about 7 cm. A linear distal tip region can be especially suitable for vascular applications involving tortuous paths. To this end, the linear distal tip region can be a flexible kink-resistant distal tip portion that is preferably atraumatic. Also seen is the radiopaque marker band 21 can be positioned about 0.25 inches from the end 17. FIG. 1 illustrates another exemplary sheath having a distal tip region 33 that is formed into an arcuate section (shown in dashed lines). The arcuate distal tip region 33 may be formed by placing the fabricated sheath under elevated temperatures while being constrained in a template of appropriate curvature, such as at an angle of about 90 degrees, although other angles are possible. For example, a flexible kink-resistant distal tip portion of about 2.5 cm with such curvature is especially suitable for use in entering the renal ostium and eases stress to the renal artery. In one example, the distal tip region is flexible to move between an arcuate configuration and a linear configuration.

Fraying of the end of the braided filaments is known to penetrate through the outer layer and/or the inner liner, thereby producing unusable sheaths. To minimize the possibility of such fraying, the braided member may be further processed before its application to the mandrel. In one example, the braided member can be subjected to a heat treatment process, such as an annealing process, in order to induce softness or improved ductility to the braided member. A more relaxed braided member reduces the risk of fraying during manufacturing.

Figure 3B:
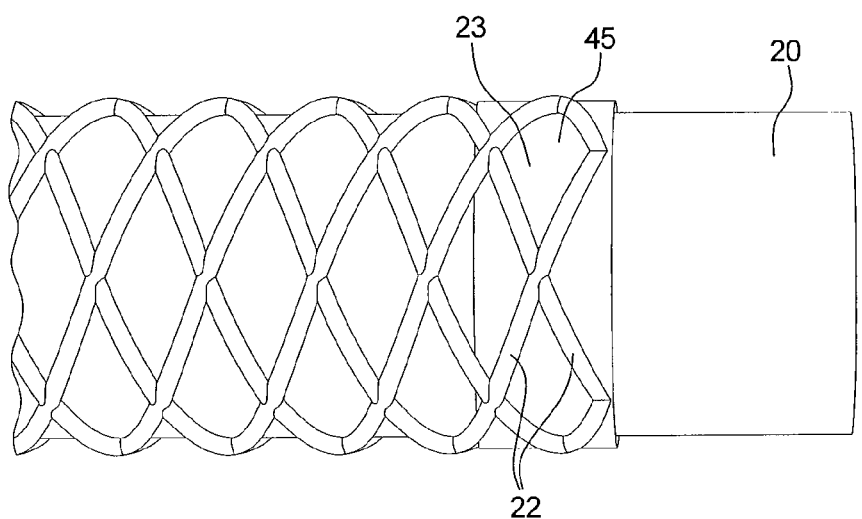
FIG. 3B is a partial side view of an end of another example medical device during its construction.
Figure 3C:
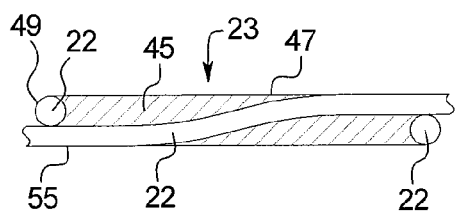
FIGS. 3C-3D illustrate the relative thickness between the braided filaments and the example braided filament securement mechanism.
Figure 3D:
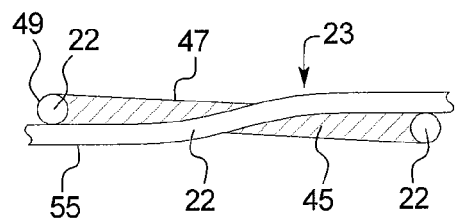

According to FIGS. 3A-3B, the braided member 16 includes a portion having a braided filament securement mechanism 45 to address such fraying. The securement mechanism 45 can fix the filaments 22 in a secured relationship relative to one another to facilitate the fixation of the ends of the braided member and prevent the ends from fraying outward and/or inward. Portions of the securement mechanism 45 can span and fill the open cells 23 that are defined by the intersecting braided filaments 22, as shown in FIG. 3B. Since the securement mechanism spans the cells to attach to the adjacent intersecting filaments, the bonding between the intersecting filaments can be enhanced along the entire segments of the filaments that define the corresponding cells. The outer surface 47 of the securement mechanism 45 can be sized to extend radially outward to a position up to, and preferably, not beyond, the outer surface 49 of the braided member 16 defined generally by the filaments 22. In other words, the thickness 51 of the securement mechanism 45 can be less than to about equal to the general thickness 53 of the braided member 16 between the inner surface 55 and the outer surface 49 of the braided member in order to not add to the overall wall thickness of the sheath. FIG. 3C illustrates one example where the outer surface of the securement mechanism 45 can form a generally smooth surface with the outer surface of the braided member. Here, the thickness of the securement mechanism 45 within the cells 23 is about the same as the thickness of the braided member, i.e., about twice the thickness of a single filament. FIG. 3D illustrates one example where the securement mechanism 45 can be thinner than in FIG. 3C. Here, the thickness of the securement mechanism 45 within the cells 23 is about the same as the thickness of a single filament such that the combined outer surfaces appear to have depressions formed therein at the center of the cells. For instance, a single filament can have a diameter of about 0.0015 to about 0.002 inches.

The securement mechanism 45 can be applied at least partially along the entire circumference of the braided member. FIG. 3B depicts the securement mechanism 45 applied along the entire circumference of the braided member to form a ring-like structure. However, the securement mechanism 45 can take on many forms and shapes, including non-geometrical shapes or patterns, zigzag pattern, or discontinuous circumferential pattern. A zigzag or discontinuous pattern can be configured to provide additional flexibility to the distal tip.

The securement mechanism 45 may include any suitable material, including but not limited to solder, thermoplastics, such as those in the nylon and urethane families, adhesives such as cyanoacrylate, or a polymer, such as PTFE, for manufacturing purposes explained further below. The securement mechanism 45 can include a radiopaque material to enhance its visibility under fluoroscopy or other imaging techniques. Nonlimiting examples of radiopaque materials include silver, gold, platinum, tantalum, or various forms of derivate alloys thereof.

According to FIG. 4, after the braided member 16 is formed, the braided member 16 can be fitted over a mandrel 110 that is operable to maintain the overall rounded shape of the braided member. The mandrel 110, which is typically metal, can have a coating 112, such as a PTFE coating, to ensure nonadhesion between the braided member 16 and the mandrel 110 during application of the securement mechanism 45. The securement mechanism 45 can be applied to the braided member 16 using any suitable techniques, including spraying the securement mechanism material onto the braided filaments or dipping the braided member into a batch of the securement mechanism material. In accordance with one aspect, at the location where the securement mechanism will be formed, the braided member may be at least temporarily held in place by a temporary bonding, such as an adhesive.

In a next step, at least a circumferential portion of the braided filaments are joined or bonded together at one or more of the intersections and the cells that are defined by the intersecting braided filaments to reduce relative movement between the braided filaments with respect to one another. The bonding may be achieved in various manners, including but not limited to thermal, mechanical and chemical techniques. The bonding can result in braided filaments that are rigidly fused together and can generally form a solid region.

In one example, a tube of fluorinated ethylene propylene (FEP) can be applied around the end of the braided member. Prior to cutting the braid, heat can be applied to the FEP tube to cause it to heat shrink onto the end of the braided member. This is believed to allow for a more even cut, while also preventing the ends of the braided member from fraying. After the FEP is removed, the braided member is slid over the inner liner and over the coiled member, if employed, at one side (proximal) of the mandrel.

In another example, the securement mechanism may comprise a polymeric tube that is wrapped around the end of the braided member. A heat source, such as convection, radiant, or radiofrequency heating techniques, can be used to melt the polymer material to flow within the open cells of the braided member. If the securement mechanism material comprises a thermoplastic such as nylon, the nylon may melt when exposed to an appropriate temperature, for example, between 300-500 degrees Fahrenheit, depending on the particular melting point of the material. The polymer material of the securement mechanism may be a higher durometer material than the outer layer material in order to provide a more rigid engagement with the filaments. The polymer material of the securement mechanism may have a higher melting temperature than the outer layer material so that the securement mechanism does not re-melt from the temperatures necessary to melt the outer layer material. The polymer material may have filaments contained therein. The filament material can be a radiopaque material, such as tungsten or other radiopaque materials described herein.

In another example, the filaments may be coated with a sufficient amount of a polymer or solder so that when heated, the polymer or solder fills the cells defined between the braided filaments and defines the securement mechanism. Examples of coated filaments are described in U.S. Patent Publication No. 2010/0016837 and U.S. Pat. No. 6,562,022, each of which is incorporated herein by reference in its entirety.

In another example, the securement mechanism 45 comprises a solder material. With reference to FIG. 4, the braided member 16 and the mandrel 110 can be positioned adjacent to a soldering iron 120 having a supply of solder 122, such as a soft solder alloy composed of, e.g., Silver-Tin, which is commercially available as All-State No. 430 from ESAB Welding (Atlanta, Ga.). The soldering iron 120 includes a heated metal tip 124 to which the solder supply 122 is coupled. The heated metal tip 124 supplies heat to the solder 126 that is supplied from the solder supply 122 so that the solder 126 can flow out from the tip 124. A flux compatible with the materials of the braided filaments and the solder may also be used to enhance the bonding of the filaments. As the solder 126 is flowing, the braided member 16 and the mandrel 110 can be rotated about the mandrel axis 130 in either direction, represented by arrows 132, to form a circumferential region and/or translated longitudinally along the axis 130 in either direction, represented by arrows 134, to form the axial length.

In FIG. 5, solidification of the solder forms the securement mechanism 45. A cleaning agent can be applied to the soldered region in order to neutralize the flux. The rate of solder flow and the rate of rotation and translation of the braided member and mandrel relative to the solder iron can be controlled to ensure that solder fills the cells 23 defined between the intersecting filaments 22 for a sufficient longitudinal distance 140 suitable for fluoroscopic visualization, such as about 3-5 mm, when the solder is a radiopaque material. In effect, the end of the braided member may be less inclined to fray open or flare in a radially outward and/or inward direction at the distal end of the braided member due to the securement mechanism. This feature may provide a significant advantage during the manufacture of the introducer sheath.

It can be appreciated that the total length of solder can be at least twice the distance 140, or about 6-10 mm, so that the braided member can be divided at the securement mechanism to form two braided segments. For example, in FIG. 5, a cutting instrument 148 can be applied to the braided member and the securement mechanism, so that at least the distance 140 is achieved. The cutting instrument 148, such as a blade or laser, is configured to cut through the solder and the filaments. In the case of a blade, the braided member and the mandrel are placed in contact with the blade and the braided member/mandrel is rotated about the axis 130 relative to the blade in order to form the cut.

Figure 6:
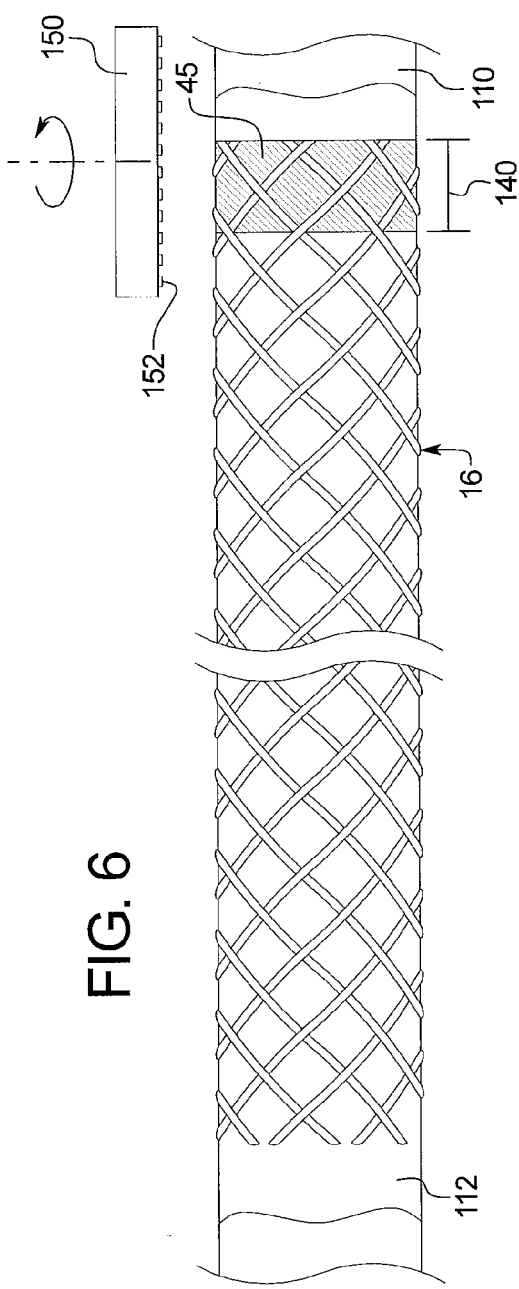
FIG. 6 is a side view of the braided member disposed over the mandrel of FIG. 5, depicting an example removing operation of a braided filament securement mechanism.

To minimize the wall thickness of the tubular body to as small as possible, the profile of the braided member 16 with the securement mechanism 45 can be reduced by removing excess securement mechanism material that extends beyond the general circumference of the outer surface of the braided member. For example, the outer surface of the securement mechanism 45 preferably does not extend beyond the outer surface defined by the filaments of the braided member 16 as described herein. In FIG. 6, excess material of the securement mechanism may be removed. For example, the braided member and the mandrel can be placed against a grinding instrument 150, such as a rotary grinding wheel that has a grinding surface 152 for removal of the desired material. For instance, the securement mechanism can be viewed under magnification for visual observation of the amount of remaining material. Preferably, under magnification the technician can observe portions of the outer surface of the filaments. Other grinding instruments can be used such as a metal file, sandpaper, or other devices that are known to remove material.

Figure 7:
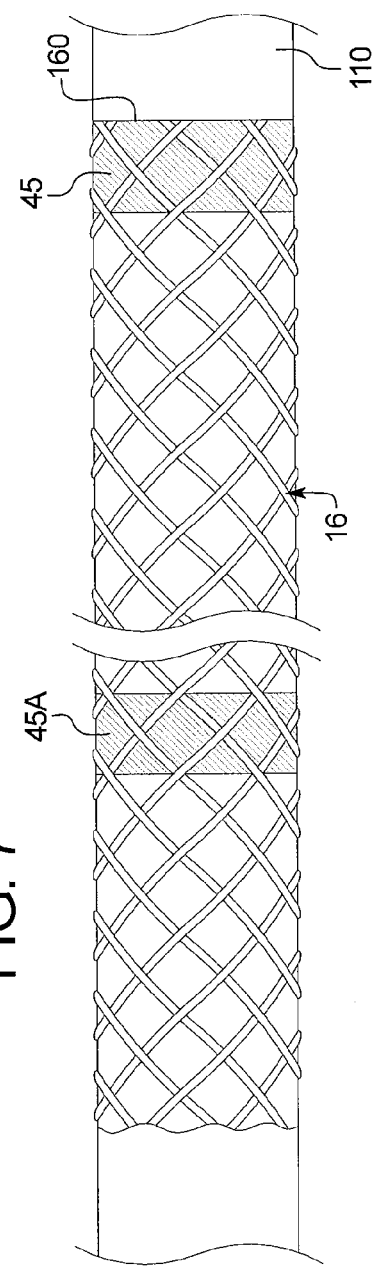
FIG. 7 is a side view of a braided member disposed over a mandrel, depicting a plurality of braided filament securement mechanisms along a braided member.

In FIG. 7, the braided member 16 can include additional securement mechanisms, such as the securement mechanism 45A at other locations besides at the distal end 160 of the braided member 16. The additional securement mechanisms can be spaced apart at regular increments for fluoroscopic indication of the insertion depth of the introducer sheath. Another application for the additional securement mechanisms is for the measurement of the lesion or the problem area within the body passageway. The proximal end (not shown) of the braided member 16 may also include a securement mechanism as described above. However, it is typical that the proximal end of the braided member is fixed within a housing of some sort such as a hub assembly, which remains outside the body during its intended use and thus is less of a concern than the distal end.

Figure 8:
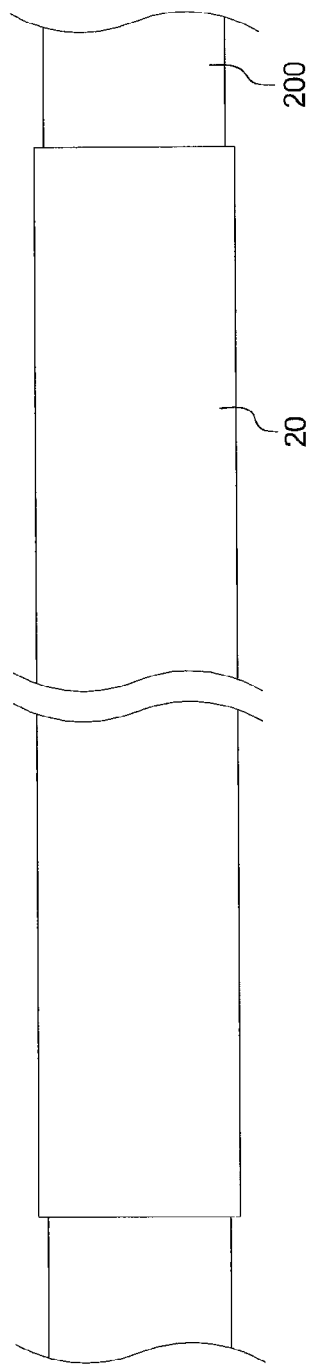

Referring now to FIGS. 8-11, exemplary method steps are described for manufacturing a medical device such as an introducer sheath. In FIG. 8, an inner tubular liner 20, if employed, may be placed over a mandrel 200. The mandrel 200 has an outer diameter that is approximate or slightly less than a desired inner diameter of the inner liner. The braided member 16, with one or more the securement mechanisms 45 formed as described above, may then be cut to the desired size.

Figure 9:
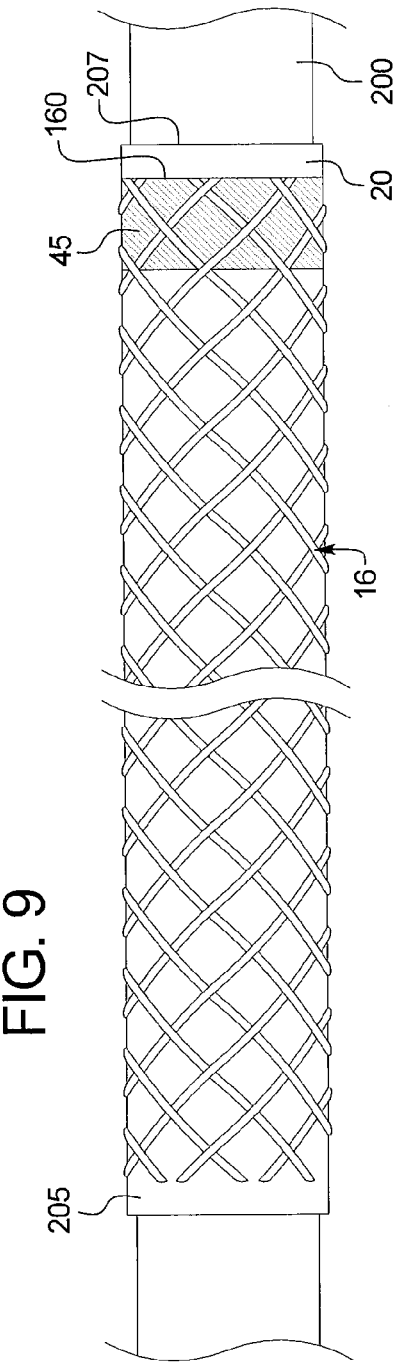

In FIG. 9, the braided member 16, with one or more securement mechanisms 45 formed as described above, then may be advanced coaxially over the outer surface 205 of the inner liner 20 and mandrel 200. In one exemplary technique, the mandrel 110 in FIG. 6, having the braided member 16 with the securement mechanism(s) disposed thereon, may be aligned with an end of the mandrel 200. The braided member 16 then may be transferred from the mandrel 110 directly over the inner liner 20. The braided member 16 may be positioned such that the distal end 160 of the braided member 16 is positioned a short distance 201 (as shown in FIG. 3A) away from the distal end 207 of the inner liner 20, as shown in FIG. 7.

According to FIG. 10, the coiled member 14 may be fitted around the braided member/inner liner/mandrel. Like the braided member 16, the distal end 211 of the coiled member 14 may be positioned a short distance from the distal end 207 of the inner liner 20. The relative distance from the distal end of the inner liner and the distal ends of the braided member and the coiled members may be same, as shown in FIG. 10, or different. In one example, the distal end of the coil is farther away from the distal end of the inner liner. In another example, the distal end of the coil is closer to the distal end of the inner liner. The coiled and/or braided members may also be positioned a short distance, the same or different distances, from the proximal end of the inner liner 20. FIG. 10 shows the turns of the coiled member 14 wrapped over the securement mechanism 45. When the coiled member is fitted over the securement mechanism, the minimum thickness of the securement mechanism allows the coiled member to fit uniformly over the braided member and not flare out.

Advantageously, since the braided member 16 includes the securement mechanism 45 at the distal end thereof as described above, the ends of the filaments are less likely to fray open or to flare radially outward and/or inward, which may facilitate insertion of the coiled member 14 over the proximal end or distal end of the braided member 16. The application of the securement mechanism 45 to the braided member 16 may substantially reduce or inhibit radial flaring at the distal end of the braided member 16, after the distal end is cut to a desired length. This arrangement may facilitate retention of the braided member 16 at an outer diameter suitable for accommodating the inner surface of the coiled member 14.

In FIG. 11, the outer tubular layer 18 then may be advanced coaxially over the reinforcement layers (braid and/or coil)/liner/mandrel. The proximal and distal ends of the outer layer 18 may be substantially aligned with the proximal and distal ends of the inner liner 20, respectively, as generally depicted in FIG. 11. To this end, regions at the proximal end and the distal end of the tubular body may not have any reinforcement layer so the proximal and distal ends remain flexible to permit tapering and flaring of the ends of the introducer sheath. Once in place, the outer layer 18 may be joined to the outer surface 205 of the inner liner 20, which preferably has been roughened, between the cells of the braided member 16 and turns of the coiled member 14.

The entire assembly is placed in a heat shrink envelope. Heat shrink enclosures for use in forming medical devices are well known in the art, with FEP being a preferred composition for use herein. Those skilled in the art will appreciate that various alternative compositions for the heat shrink envelope would also be suitable for use in forming the tubular body sheath, as long as the melt temperature of the material used for the outer layer is lower than that of the heat shrink enclosure. Heat may be applied at a suitable temperature that is within the processing temperature range of the outer tube material, such as, e.g., about 300-500 degrees Fahrenheit. In one example, the heat shrink enclosure and contents are placed in an oven and heated (typically at about 385° F. (196° C.) when FEP is used as the heat shrink and a polyether block amide is used as an outer layer material) for a suitable period of time to melt the outer layer material. This causes the outer layer material to melt and flow between the cells of the braided member 16 and the turns of the coiled member 14, being urged thereinto by shrinking of the heat shrinkable tube. The melted outer layer material can mechanically connect to the radially outer surface of the inner liner 20. The outer surface of the inner liner 20 may be chemically etched or mechanically roughened in well-known manner for enhancing bonding between the inner liner and the outer layer material. After removal from the oven, the entire assembly is cooled, and the heat shrink envelope is cut away. Such a heat shrink technique is described in greater detail in the '304 patent.

Once the process is completed, the heat shrinkable tubing may be split from around the outer layer 18, the mandrel 200 may be removed from within the lumen of the inner liner 20, and the tubular body is in the form shown from the partial side-sectional view in FIG. 1. Since the heat formable material of the outer layer 18 may also be self-leveling, it may provide a uniform outer diameter surface for the tubular body 11. Subsequently, other manufacturing steps may be employed to complete the construction of the introducer sheath 20, such as thermally bonding a distal tip portion to a distal end of the tubular body and/or a hub assembly to a proximal end of the tubular body, as generally set forth in the '304 patent and the '514 publication.

Various technical advantages may be achieved by placing the braided member 16 beneath the coiled member 14. For example, the surface area of the open cells between the filaments of the braided member 16 may be greater than the surface area of the open spacing between the turns of the coiled member 14, which may provide an increased surface area for directly bonding the outer layer 18 to the inner liner 20 during the heat shrink process. If the bond between the outer layer 18 and the inner liner 20 is enhanced, then the overall structural integrity of the tubular body 11 may be improved. Alternatively, the braided member 16 may be disposed above the coiled member 14 and within the outer layer 18, in which case it may be desirable to increase the spacing between turns of the coiled member to provide an increased area for directly bonding the outer layer to the inner tube liner. However, it will be apparent that the techniques described above to stabilize a circumferential section of filaments with a securement mechanism may be used in any sheath construction having a braided member, regardless of whether the coiled member is used in conjunction with the braided member.

Introducer sheaths may be formed to have any length required to fulfill its intended purposes. In most cases, the sheath will have a length between about 40 and 125 cm, and most generally, between about 70 and 100 cm. Generally, the lengths of the inner liner 20 and the outer layer 18 are the same. For an exemplary sheath of 70-100 cm length, the distal portion, for example the distal 30-60 cm, may be covered with a conventional hydrophilic coating, such as AQ® hydrophilic coating. In addition, if desired, the outer layer 18 can comprise two or more discrete longitudinal segments of differing durometer. Making the distal portion of the outer layer from a lower durometer material than that from which the proximal portion is made yields a tubular member whose distal portion is more flexible than the proximal portion. This arrangement is described in greater detail in the incorporated-by-reference '514 Publication.

The dimensions (for example, the thickness) of the various elements mentioned above should be selected in view of the proposed use of the introducer sheath. It is believed that the selection of such dimensions will lie within the level of skill in the art, once benefit of the present disclosure is had. While a modest amount of trial-and-error may be needed to obtain optimal dimensions, it is believed that any required experimentation will not be undue. Details of the construction or composition of the various elements of the introducer sheath not otherwise disclosed are not believed to be critical to the present invention, so long as the recited elements possess the strength or mechanical properties needed for them to perform as required. Many such details not described herein are recited in detail in the incorporated-by-reference '304 Patent and the '514 Publication. Additional details of construction are believed to be well within the ability of one of ordinary skill in the art.

In one example of use, a 4 to 8 French sized introducer sheath includes an arcuate distal tip region, a braided member, a coiled member, and a securement mechanism formed from a radiopaque solder material such as shown in FIG. 3A. The distal end of such introducer sheath is initially inserted through a body opening previously formed, e.g., by the well-known Seldinger technique. The introducer sheath is advanced, typically over a wire guide (not shown) through the body passageway until the distal end reaches the target site. The distal end of the wire guide can then be retracted within the sheath so that the distal tip region is permitted to assume its arcuate shape. The end user can then maneuver (i.e., applying torque to) the proximal end of the sheath so that the distal tip region can be placed at a branching vessel, such as the renal arteries. Once the distal tip is positioned within the branching vessel, the wire guide can be advanced through the branching vessel to the target site. Thereafter, the sheath can be moved along the wire guide to the target site within the branching vessel.

The tube can be configured for surgical use itself or can be incorporated into a device which also includes other apparatus having surgical utility. One example of the former is in a balloon catheter, in which the tube is configured (particularly shaped and adapted) as a catheter shaft carrying on it an inflatable balloon. Balloon catheters are useful for performing angioplasty and for the deployment of a stent for preventing stenosis (closure) of a body passage, e.g., a blood vessel. Another example of the former is in a diagnostic, infusion or drainage catheter, in which the tube is configured as a catheter for the delivery of a diagnostic fluid to the patient (for example, for imaging); for the delivery of a therapeutic fluid to the patient (either short or long term); or for the removal of a fluid from the patient. Examples of devices including apparatus in addition to the tube are endoscopes, laparoscopes, arthroscopes or the like, and guide catheters and introducer sheaths (percutaneous or otherwise), through which a guide wire or other surgical device is introduced into the patient.

It is therefore intended that the foregoing detailed description be regarded as illustrative rather than limiting, and that it be understood that it is the following claims, including all equivalents, that are intended to define the spirit and scope of this invention.

The invention claimed is:

1. A tubular body for a medical device comprising:
a tubular inner liner having an outer surface;
a braided member disposed along the outer surface of the inner liner, the braided member having a proximal end and a distal end, and including a plurality of intersecting filaments and a plurality of cells defined by the intersecting filaments, the braided member comprising a braided filament securement mechanism disposed along a circumferential region located at the distal end of the braided member and configured to inhibit relative movement of the filaments, the securement mechanism attached to portions of the filaments and spanning the cells that correspond to the circumferential region, wherein the securement mechanism fills one or more of the cells that correspond to the circumferential region, wherein an outer surface of the braided member is positioned at or beyond an outer surface of the securement mechanism, the securement having a thickness which is not greater than a thickness of the braided member; and
an outer jacket positioned longitudinally around the braided member, and connected to said inner liner.

2. The tubular body of claim 1, wherein the securement mechanism comprises a radiopaque material.

3. The tubular body of claim 1, further comprising a coiled member having a plurality of turns disposed over at least a portion of the braided member and the inner liner.

4. The tubular body of claim 1, further comprising a coiled member having a plurality of turns disposed over the inner liner and underneath at least a portion of the braided member.

5. The tubular body of claim 1, wherein the inner liner comprises a lubricious fluoropolymer.

6. The tubular body of claim 5, wherein the outer surface of the inner liner comprises a roughened outer surface, and wherein the outer jacket is bonded to the inner liner at the roughened outer surface.

7. The tubular body of claim 1, wherein the securement mechanism comprises a radiopaque solder material.

8. The tubular body of claim 7, wherein the braided member further comprises multiple securement mechanisms, the securement mechanisms being axially spaced from one another at regular intervals.

9. The tubular body of claim 1, wherein the outer jacket comprises a heat formable polyamide material.

10. The tubular body of claim 1, wherein distal ends of the respective outer jacket and inner liner extend distally beyond the distal end of the braided member to form a nonbraided region in the tubular body.

11. The tubular body of claim 1, wherein said securement mechanism comprises a polymer having filaments comprising a radiopaque material.

12. An introducer sheath comprising:
a tubular inner liner having an outer surface;
a braided member disposed along the outer surface of the inner liner, the braided member having a proximal end and a distal end, and including a plurality of intersecting filaments and a plurality of cells defined by the intersecting filaments, the intersecting filaments defining an outer surface and an inner surface of the braided member, the braided member comprising a braided filament securement mechanism disposed along a circumferential region of the braided member and configured to inhibit relative movement of filament ends, wherein the thickness of the securement mechanism is sized to fit between the outer and inner surfaces of the braided member, wherein the securement mechanism comprises a radiopaque solder rigidly fused to portions of the filaments and spanning the cells that correspond to the circumferential region, wherein the securement mechanism fills one or more of the cells that correspond to the circumferential region, the securement having a thickness which is not greater than a thickness of the braided member;

a coiled member disposed along the outer surface of the inner liner; and an outer jacket positioned longitudinally around the braided member, and connected to said inner liner.

13. The introducer sheath of claim 12, wherein the securement mechanism is disposed along a distal region of said sheath, the distal region being movable between an arcuate configuration and a linear configuration.

14. The introducer sheath of claim 12, further comprising a plurality of securement mechanisms axially spaced from one another at regular intervals.

* * * * *